US00PP23085P2

(12) United States Plant Patent
Korlipara

(10) Patent No.: US PP23,085 P2
(45) Date of Patent: Sep. 25, 2012

(54) *ECHINACEA* NAMED 'SECRET DESIRE'

(50) Latin Name: ***Echinacea* spp.**
Varietal Denomination: Secret Desire

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 42 days.

(21) Appl. No.: 13/066,145

(22) Filed: Apr. 6, 2011

(51) Int. Cl.
*A01H 5/00* (2006.01)

(52) U.S. Cl. ..... Plt./428

(58) Field of Classification Search ..... Plt./428
See application file for complete search history.

*Primary Examiner* — Susan McCormick Ewoldt
(74) *Attorney, Agent, or Firm* — Klarquist Sparkman, LLP

(57) ABSTRACT

A new and distinct *Echinacea* plant named 'Secret Desire' characterized by enlarged disc florets forming an anemone-type inflorescence, very large inflorescences, ray and disc florets a two-toned pink and soft orange color, a medium sized, upright habit with good branching, and excellent vigor.

1 Drawing Sheet

Botanical denomination: *Echinacea* spp.
Variety designation: 'Secret Desire'.

BACKGROUND OF THE INVENTION

The present invention relates to a new and distinct cultivar of *Echinacea* and given the cultivar name 'Secret Desire'. *Echinacea* is in the family Asteraceae. This new cultivar is a third generation seeding originating from a planned breeding program using *Echinacea purpurea* 'Razzmatazz' (U.S. Plant Pat. No. 13,894) as the seed parent in the original cross and unnamed proprietary, unreleased interspecific hybrids for the pollen parent. The exact parents of this selection are unknown, unnamed, proprietary plants.

Compared to *Echinacea purpurea* 'Razzmatazz' (U.S. Plant Pat. No. 13,894), the seed parent in the original breeding line, the new variety has larger flowers that are a multicolored orange rather than pink.

Compared to *Echinacea* 'Hot Papaya' (U.S. Plant Pat. No. 21,022), the new cultivar has larger and softer orange colored flowers.

This new *Echinacea* cultivar is distinguished by:

1. enlarged disc florets forming an anemone-type inflorescence,
2. very large inflorescences,
3. ray and disc florets a two-toned pink and soft orange color,
4. a medium sized, upright habit with good branching, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the inflorescences and habit of *Echinacea* 'Secret Desire' as a two-year-old in the field in full sun in early July in Canby, Oreg.

DETAILED PLANT DESCRIPTION

The following is a detailed description of the new *Echinacea* cultivar based on observations of a two-year-old specimens growing in the two gallon pots outdoors in the nursery in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type*.—Herbaceous perennial.
*Hardiness*.—USDA Zones 4 to 9.
*Size*.—Grows to about 94 cm wide and 76 cm tall to top of inflorescences.
*Form*.—Basal clump, with about 30 stems from the base.
*Vigor*.—Excellent.
*Roots*.—Fibrous, with many downward growing and few laterals, ivory in color, Yellow White 158D, roots develop easily from cuttings from the crown.

Stem (flowering):

*Type*.—Ascending, with 1 to 5 flowers per stem.
*Size*.—To 92 cm tall to a terminal inflorescence and 9 mm wide at base.
*Internode length*.—4.5 cm to 9 cm.
*Surface texture*.—Strigose.
*Color*.—Brown 200A to Yellow Green 144A mottled Brown 200A.

Leaf (basal):

*Type*.—Simple.
*Shape*.—Lanceolate.
*Arrangement*.—Basal.
*Blade size*.—Grows to 17 cm long and 5.5 cm wide.
*Margins*.—Coarsely serrate.

*Apex*.—Acuminate.
*Base*.—Attenuate.
*Surface texture*.—Strigose on both sides.
*Venation*.—Pinnate, with 3 main veins.
*Color*.—Topside, Green N137B, bottom side closest to Yellow Green 147B.
*Petiole description*.—Grows to 28 cm long and 3 mm wide, sparsely hirsute, Yellow Green 146B, except base where Greyed Purple 187B.

Leaf (stem):
*Type*.—Simple.
*Shape*.—Lanceolate to elliptic.
*Arrangement*.—Alternate.
*Blade size*.—Grows to 14 cm long and 4.5 cm wide.
*Margins*.—Somewhat undulate, irregularly serrate.
*Apex*.—Acuminate.
*Base*.—Attenuate.
*Surface texture*.—Strigose on both sides.
*Venation*.—Pinnate, with 3 main veins from the base.
*Color*.—Topside, Yellow Green 146A, bottom side closest to Yellow Green 147B.
*Petiole description*.—On lowermost leaves only, clasping, grows to 7 cm long and 5 mm wide above the clasp, hirsute, Yellow Green 146C on back and 146C tinted Greyed Purple 187B.

Inflorescence:
*Type*.—Composite on terminal stalked heads.
*Number of flowering stems per plant*.—About 30.
*Flowering stem*.—Grows to 76 cm tall from the base of the plant to the terminal inflorescence and can grow to 21 cm long from the top stem leaf to the base of an inflorescence; branched, with 1 to 5 inflorescences per stem; diameter growing to 8 mm wide near the inflorescence; strigose; Yellow Green 144A mottled Brown 200A.
*Size*.—Grows to 9 cm wide and 6 cm deep as disc enlarges.
*Form*.—Ray florets held slightly reflexed, mature disc is conic.
*Immature inflorescence*.—3.5 cm wide and 1.8 cm deep, ray florets held upright and rolled up so only the back color shows, Greyed Red 180D with Green Yellow 1C on tip, disc color Greyed Purple 187A in the foreground and Yellow Green 144A in the background.
*Ray florets*.—Without pistil or stamen, about 19 in number, grow to 40 mm long and 9 mm wide, oblanceolate with the tip two to three toothed (each acute), entire margins, base attenuate, glabrous on both sides; top and bottom side Greyed Purple 186C at the base half blending to Yellow Orange 21C at the apex.
*Disc*.—Flat becoming conic, becoming 30 mm deep and 65 mm wide with maturity, overall color is Greyed Purple 186B on top to Greyed Orange 168C on bottom.
*Disc florets*.—About 400 in number, each with 1 pistil and 4 stamen, grow to 25 mm long and 6 mm wide, each with one persistent, very stiff linear bract (14 mm long with the tip Greyed Purple 187B to Yellow Orange 22A to Yellow Green 144A in middle, then White NN155D on bottom ⅓); showy 2 to 3 cleft corollas grow to 21 mm long and 6 mm wide, tubular on the bottom, glabrous on both sides, topside color Greyed Purple 186B maturing to Yellow Orange 22A, back side color Greyed Purple 186C maturing to Yellow Orange 22B; pistil grows to 9 mm long, ovary 3 mm long, White NN155D, style 3 to 6 mm long Greyed Purple 186D, 2-branched stigma spreading, Greyed Purple 187A; stamen 4 mm long, anthers 1.5 mm long and Greyed Purple N186A, filaments 2.5 mm long, White 155A, no pollen, male sterile.
*Phyllaries*.—In 4 leafy series, area 38 mm wide and 9 mm deep, lobes lanceolate in shape, reflexed slightly, grow to 10 mm long and 5 mm wide, Yellow Green 147B, margins strigose, tip acute, strigose on both sides.
*Receptacle*.—Grows to 16 mm wide and 16 mm deep, White 155A.
*Bloom period*.—July through October in Canby, Oreg.
*Fragrance*.—Good, floral.
*Lastingness*.—Each inflorescence lasts about two weeks in Canby, Oreg.

Seeds: None seen.
*Fertility*.—Poor.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

* * * * *

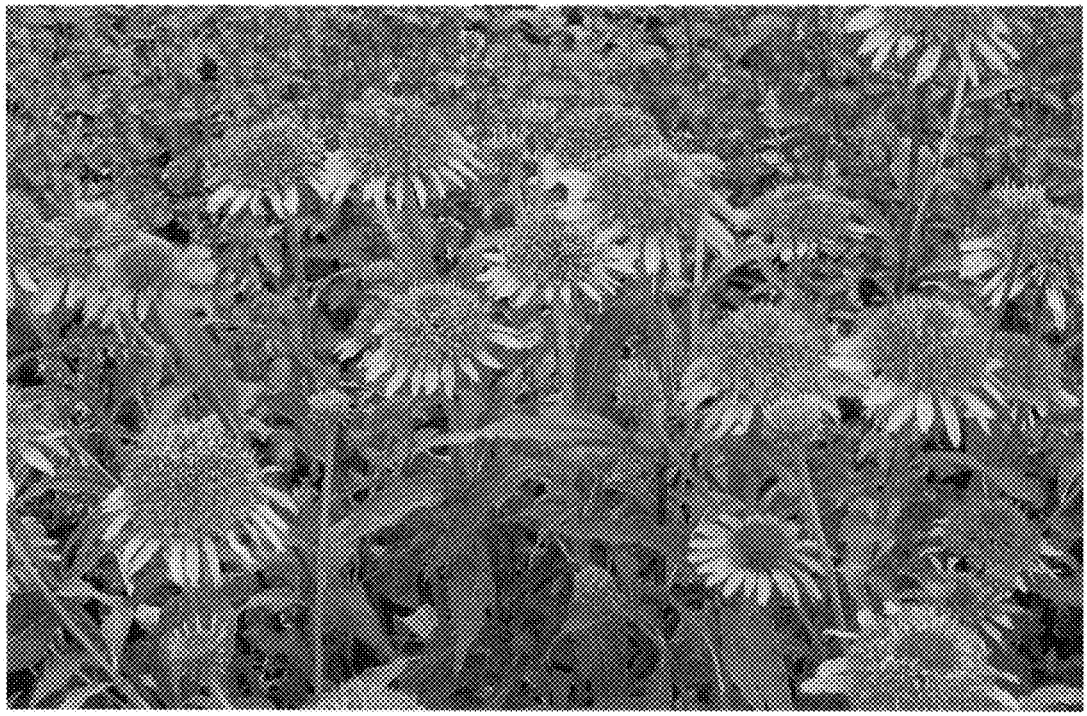

UNITED STATES PATENT AND TRADEMARK OFFICE

CERTIFICATE OF CORRECTION

PATENT NO. : PP23,085 P2
APPLICATION NO. : 13/066145
DATED : September 25, 2012
INVENTOR(S) : Harini Korlipara It is certified that error appears in the above-identified patent and that said Letters Patent is hereby corrected as shown below:

On the Title page, item [54] and in the Specification, column 1, in the Title:

"*ECHINACEA* NAMED 'SECRET DESIRE'" should be --*ECHINACEA* PLANT NAMED 'SECRET DESIRE'--.

Signed and Sealed this
Third Day of September, 2013

Teresa Stanek Rea
*Acting Director of the United States Patent and Trademark Office*